United States Patent [19]
Dow

[11] Patent Number: 5,903,921
[45] Date of Patent: May 18, 1999

[54] FOLDABLE HEADGEAR AND METHOD OF DISPLAYING AND STORING THE HEADGEAR

[76] Inventor: Mary Dow, 8955 S. Ridgeline Blvd. Suite 110, Littleton, Colo. 80126

[21] Appl. No.: 09/152,319

[22] Filed: Sep. 14, 1998

[51] Int. Cl.$^6$ ........................................................ A61F 9/00
[52] U.S. Cl. .................................. 2/12; 2/195.2; 2/195.5; 2/200.1
[58] Field of Search ........................... 2/12, 175.1, 175.5, 2/195.1, 195.2, 195.5, 200.1

[56] References Cited

U.S. PATENT DOCUMENTS 4,096,589  6/1978  Goldstein ..................................... 2/12

*Primary Examiner*—Diana L. Oleksa
*Attorney, Agent, or Firm*—Edwin H. Crabtree; Ramon L. Pizarro; Donald W. Margolis

[57] ABSTRACT

A high quality, ultra-lightweight headgear and method of displaying and storing the headgear in a rolled up format. The headgear is adapted for folding and rolling into a tight compact unit for ease in packaging, product display, travel and storage. The headgear, when unrolled and unfolded, returns to its original and natural shape maintaining its rigidity and new appearance. The headgear may be a visor, ball cap and the like and is made of cloth fabric with a fabric covered soft bill of different shapes. The bill is characterized by being made of closed cell, chemically crosslinked, polyolefin foam with an average cell size of not more than, 0.008 inches and a density range of 5 to 12 pcf. The bill, by the nature of the polyolefin foam construction, won't break or crease when folded or crushed. The bill has a thickness in a range of $3/32$ to $1/8$ inches and a compression set in a range of 6 to 10% of its thickness. The closed cell polyolefin foam structure of the bill is more rigid and has a higher tensile strength and modulus which makes it a firmer cap bill and also allows its use in a much thinner skiving without the bill having a floppy appearance. The headgear also includes hook and loop fasteners which allow the item to be adjustable to any size head. Further, the headgear includes a headband covered with cloth fabrics The headband is made of an open cell foam material and is designed to absorb perspiration and be self wicking.

15 Claims, 2 Drawing Sheets

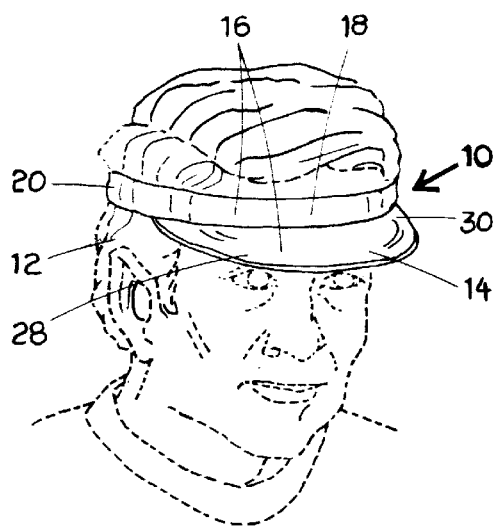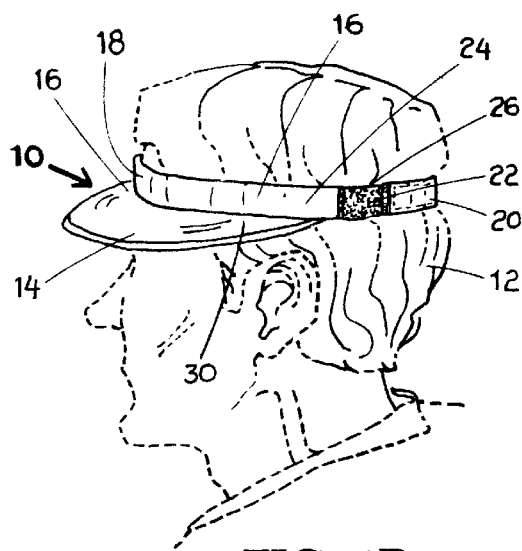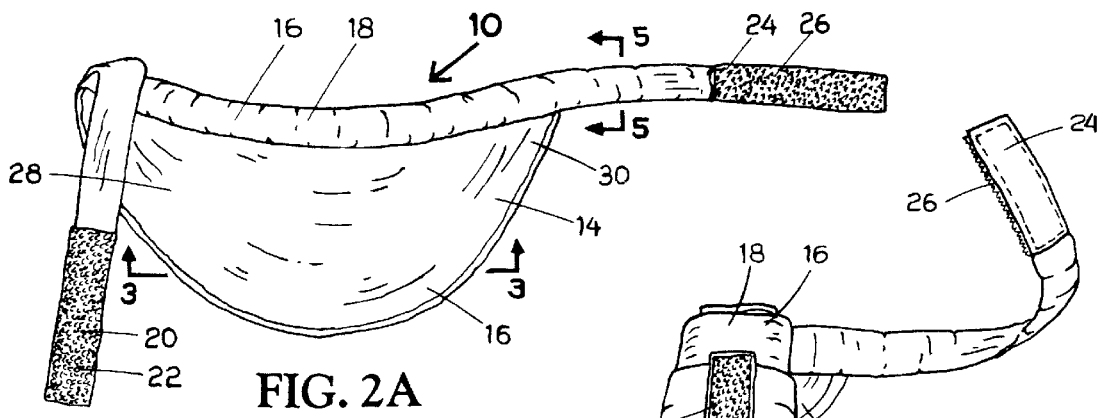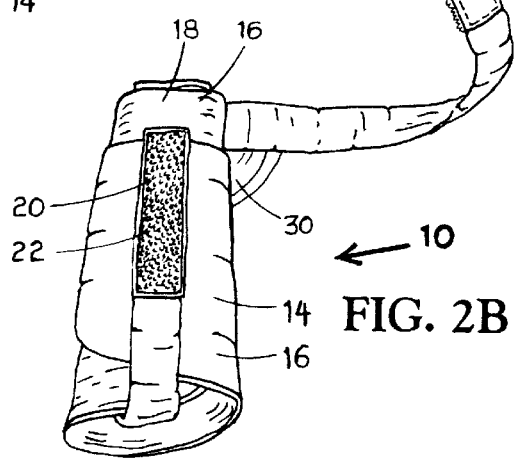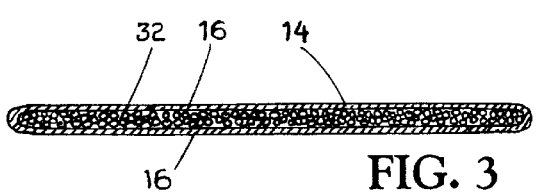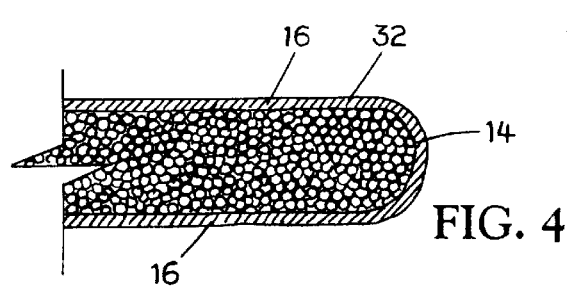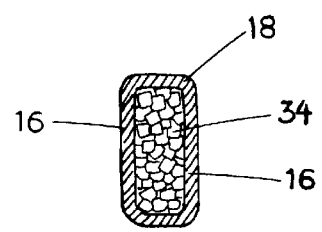

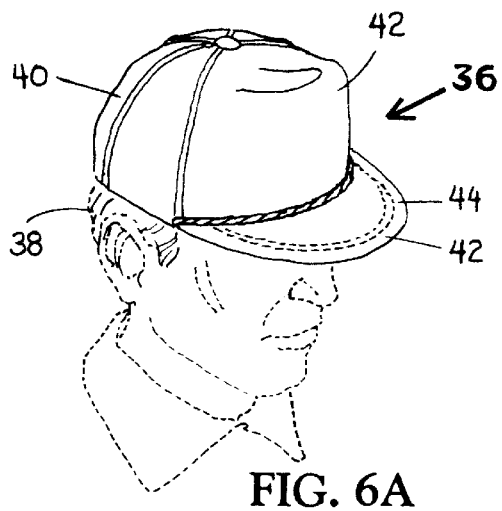
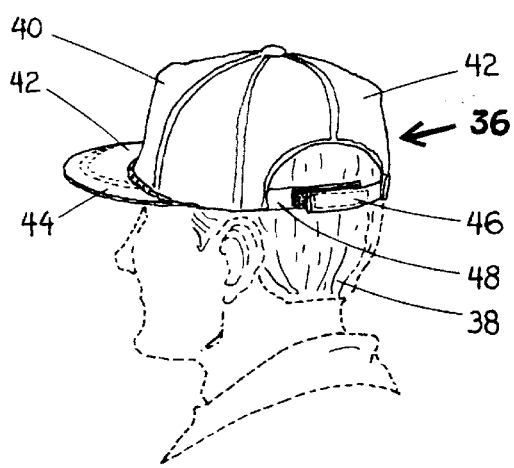
FIG. 6A  FIG. 6B
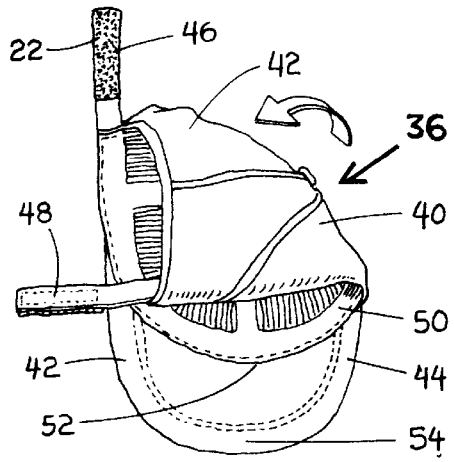
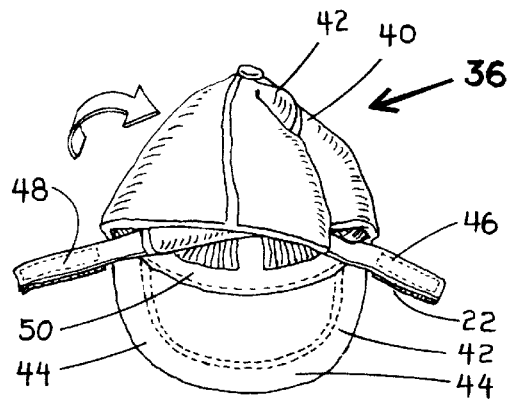
FIG. 7A  FIG. 7B
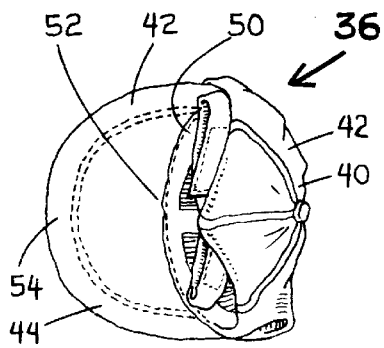
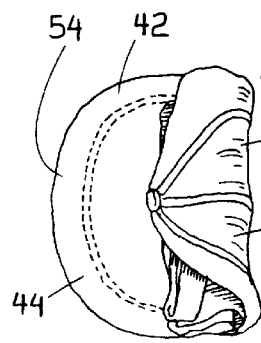
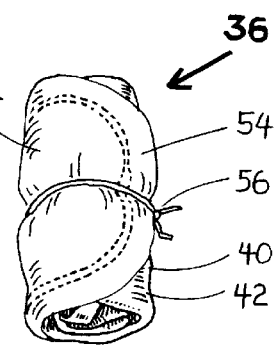
FIG. 8A  FIG. 8B  FIG. 8C

FOLDABLE HEADGEAR AND METHOD OF DISPLAYING AND STORING THE HEADGEAR

BACKGROUND OF THE INVENTION (a) Field of the Invention

This invention relates to headgear such as ball caps and visors and more particularly, but not by way of limitation, to caps and visors having a soft foam bill which can be folded and rolled into a compact form and unrolled returning to its original shape and appearance.

(b) Discussion of Prior Art

In today's market, typical headgear such as hard billed caps and visors do not allow a user to roll or fold the item into a compact unit for ease in storage. For example, a typical baseball cap has a hard bill and while the bill can be bent into an arch-like shape, the cap is not designed for folding and rolling up into a tight compact form during travel or storage. Also, there are various types of rubber visors that can be rolled up into a rolled or folded unit, but the material used in these type products is best described as "limp" and the products are made cheaply with no concern for quality and appearance over the life of the articles In U.S. Pat. No. 5,754,983 to Landers, a sport cap is disclosed with a visor made of a thick-walled neoprene foam rubber. The visor is described as having form stability, soft and pliable and can be transported while crushed together and return to its original form when placed on the head of the user. While this sport cap with a visor of neoprene foam rubber may appear to be similar to the subject invention, it does not have the unique properties and advantages of the polyolefin resin foam incorporated into a soft bill of the headgear described herein.

While there are many types of visors and ball caps that would outwardly appear to be similar to the subject invention, none of the above mentioned prior art visors and caps provide the unique combination of structure and material selection for providing an ongoing attractive appearance with the ability to be folded and rolled into a compact unit for display, storage and travel purposes.

SUMMARY OF THE INVENTION

In view of the foregoing, it is a primary object of the subject invention to provide a high quality and ultra-lightweight headgear which is attractive in appearance and maintains its new appearance over a period of use.

Still another object of the invention is the headgear can readily be adapted for folding and rolling into a compact unit for packaging, product display, during travel and storage. The headgear, when unrolled and unfolded, returns to its original and natural shape maintaining its rigidity and new appearance. The headgear includes a fabric covered soft bill made of polyolefin resin foam. The soft bill will not crease or break when folded or crushed. The soft bill, by the nature of the polyolefin resin foam, will not collapse or droop due to the density of the foam material unlike rubber and neopryne. Also, because of the closed cell foam, the headgear is waterproof and will float thereby making it suitable for water sports.

Yet another object of the headgear is it may be made in the form of visor, ball cap and the like. The headgear is machine washable, soft and has a fabric covered open cell foam headband. The open cell foam is designed to be self wicking and absorb perspiration.

Still another object of the invention is the use of hook and loop fasteners on the headband of the product for adjusting the item to different size heads.

The subject invention is made of cloth fabric with a soft crescent shaped bill or a variety of bill shapes. The bill is made of closed cell, polyolefin foam with an average cell size of not more than, 0.008 inches and a density range of 5 to 12 pcf. The bill, by the nature of the polyolefin foam construction, won't break or crease when folded or crushed. Also, the bill has a thickness in a range of 3/32 to 1/8 inches and a compression set in a range of 6 to 10% of its thickness. The closed cell polyolefin resin foam structure of the bill makes it more dense while allowing much thinner skiving without the bill having a floppy appearance. Also, by the nature of the closed cell foam, the bill is waterproof. The headgear can be displayed or stored with the cap or visor straps folded and the bill rolled end to end or from side to side into a tight roll and secured to the cap or visor straps. The polyolefin foam soft bill and cloth fabric allow the headgear to be compressed, folded and rolled into a compact unit. The headgear also includes hook and loop fasteners which allow the item to be adjustable to any size head. Further, the headgear includes a headband covered by cloth fabric. The headband is made of an open cell foam material and is designed to absorb perspiration and be self wicking.

These and other objects of the present invention will become apparent to those familiar with the different types of headgear such as ball caps and visors when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1A is a perspective view of the subject invention shown as foldable visor secured around a front portion of a head of a human model.

FIG. 1B is another perspective view of the foldable visor as shown in FIG. 1A and secured around a rear portion of the head of the human model.

FIG. 2A is a top view of the foldable visor in an unfolded position and ready for folding and prior to storage or for display.

FIG. 2B is a top view of the visor in one of the visor straps folded and the soft crescent shaped bill rolled into a tight compact unit and ready for storage or for display.

FIG. 3 is a sectional view of the soft polyolefin foam bill taken along lines 3—3 shown in FIG. 2A.

FIG. 4 is a greatly enlarged sectional view of a portion of the polyolefin foam bill.

FIG. 5 is a sectional view of the headband with open cell foam and fabric cover taken along lines 5—5 shown in FIG. 2A.

FIG. 6A is a perspective view of the subject invention shown as ball cap and secured around a front portion of a head of a human model.

FIG. 6B is another perspective view of the ball cap as shown in FIG. 6A and secured around a rear portion of the head of the human model.

FIG. 7A is a rear view of the ball cap with the headcover of the ball cap in a half folded position.

FIG. 7B is a rear view of the ball cap with the headcover in a folded position forming a triangular shape.

FIG. 8A is a rear view of the ball cap with the headcover rolled next to the soft bill of the ball cap.

FIG. 8B is a rear view of the ball cap with the headcover and a portion of the soft bill partially in roll.

FIG. 8C illustrates the ball cap in a fully rolled position and ready for storage or display.

DESCRIPTION OF THE PREFERRED EMBODIMENTS

In FIG. 1A, a perspective view of the subject headgear shown as a foldable and rollable visor. While a visor and a ball cap are shown in the drawings, it should be kept in mind that the headgear maybe of various designs and shapes without departing from the spirit and scope of the invention as described. Also, it should be mentioned that the subject inventor is marking the headgear nationwide and having a brand name of "SCRUNCHCAP™" . Of interest, the new headgear as described is advertized by stating "Roll it!, Scrunch it!, Stuff it in your bag . . . "

The visor is illustrated having general reference numeral 10. The visor 10 is shown secured around a head 12 of a human model. The visor 10 broadly includes a soft foam bill 14 covered with a cloth fabric 16. The bill may have a crescent shape and other desired shapes depending on the style and type of headgear. The bill 14 is attached to a self wicking foam headband 18. The headband 18 is also covered with a cloth fabric 16. The headband 18 includes a first end 20 having hook fasteners 22 thereon and a second end 24 having loop material 26 thereon. The loop material 26 and the hook fasteners 22 are shown in FIG. 2A.

FIG. 1B illustrates a perspective view of the foldable visor 10 secured around a rear portion of the head 12 of the human model. The hook fasteners 22 and the loop material 26 on the first and second ends 20 and 24 of the headband 18 allow for quick adjustment on different size heads.

FIG. 2A illustrates a top view of the foldable visor 10 in an unfolded and unrolled position and ready for folding and rolling. In this view, the first end 20 of the head band 18 has been folded perpendicular to the length of the head band 18 and adjacent a first side 28 of the soft foam bill 14. In operation, the first end 20, the head band 18 and the bill 14 are now rolled together in a tight compact unit from left to right until reaching a second side 30 of the bill 14.

FIG. 2B illustrates the visor 10 rolled into a unique and secure compact unit ready for packaging, display or storage. In this drawing the rolling is completed by the second end 24 of the head band 18 folded over the rolled up bill 14 and head band 18 with the loop material 26 engaging the hook fasteners 22 of the second end 24 of the head band 18 thus completing the method of storing or displaying of the visor 10.

It should be noted that when the visor 10 is unrolled for use, the soft foam bill 14 is made of a soft polyolefin resin foam material that by memory quickly retains its original shape as shown in FIGS. 1A and 1B.

In FIG. 3, a sectional view of the soft polyolefin foam bill 14 is shown taken along lines 3—3 shown in FIG. 2A. The bill 14 is cover by the cloth fabric 16 with the fabric 16 sewn thereon using conventional sewing methods.

In FIG. 4, a greatly enlarged sectional view of a portion of the polyolefin resin foam bill 14 is shown. The polyolefin resin foam is depicted in the drawing having reference character 32. The polyolefin resin foam includes a family of members such as different density of polythelene, polyproplene and ethylene vinyl acetate. The properties of the selected polyolefin resin foam are key to the headgear described herein. For example, the polyolefin resin foam 32 used in the soft bill 14 is closed cell and has an average cell size of not more than, 0.008 inches. The resin foam 32 has a density range of 5 to 12 pcf (ASTM D3575). The ideal density for the bill 14 of the headgear is 10 pcf. The bill 14, by the nature of the polyolefin foam construction, won't break or crease when folded or crushed. The bill 14 also has a thickness in a range of 3/32 to 1/8 inches and a compression set in a range of 6 to 10%(ASTM D3575) of it's original thickness. The ideal compression set for the headgear is 8.2.

In FIG. 5, an enlarged sectional view of the headband 18 is illustrated and taken along lines 5—5 shown in FIG. 2A. and covered with cloth fabric 18. Inside the headband 18 is an open cell foam 34. The headband 18 with the open cell foam 34 is designed to absorb perspiration and be self wicking when in use. The open cell foam 34 has a density range of 2 to 3 pcf (ASTM D3574) and a compression set of 10% (ASTM D3574) maximum of the foams original thickness.

In FIG. 6A, a perspective view of another embodiment of the subject headgear is shown as a ball cap having general reference numeral 36. The ball cap 36 is secured around a head 38 of a human model. The ball cap 36 includes a head cover 40 made of cloth fabric 42. Also, the ball cap 36 includes a soft foam bill 44 attached to the head cover 40. The bill 44 is also covered with the cloth fabric 42. The head cover 40 includes a first head strap 46 with hook fasteners 22 thereon and a second head strap 48 with loop material 26 thereon. The head straps 46 and 48 are used for adjusting the head cover 40 to different sizes of heads. The head straps 46 and 48 are shown in FIG. 6B. The head straps when connected with the hook fasteners 22 and loop material 26 hold the rolled bill in place for compact display.

In FIG. 6B, another perspective view of the ball cap 36 is shown similar to FIG. 6A and secured around a rear portion of the head 38 of the human model. In this view, The first head strap 46 is shown secured to the second head strap 48 using the hook and loop fasteners 22 and 26.

FIG. 7A illustrates a rear view of the ball cap 36 with the head cover 40 of the ball cap 36 in a half folded position. Also the ball cap 36 is shown with a headband 50. The headband 50 may or may not include an open cell foam 34 similar to the headband 18 discussed above.

FIG. 7B illustrates a rear view of the ball cap 36 with the head cover 40 in a folded position forming a triangular shape.

FIG. 8A shows a rear view of the ball cap 36 and in this example, the head cover 40 has been rolled next to a rear edge 52 of the soft bill 44 and next to the headband 50 of the ball cap 36. As mentioned above, by the nature of the physical structure of the polyolefin resin foam used in the construction of the soft bill 44, which is constructed the same as the soft bill 14, the soft bill 44 can be easily rolled and unrolled retaining its original shape.

In FIG. 8B, another rear view of the ball cap 36 with the head cover 40 is illustrated with a portion of the soft bill 44 partially in roll and being rolled toward a front edge 54 of the soft foam bill 44.

In FIG. 8C, the ball cap 36 has been completely rolled into a tight compact unit for packaging, display or storage. The head cover 40 and the soft bill 44 are held together in the tight roll as shown by securing a removable tie 56 therearound.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed, except as precluded by the prior art.

The embodiments of the invention for which an exclusive privilege and property right is claimed are defined as follows.

I claim:

1. A high quality, ultra-lightweight headgear adapted for folding and rolling into a tight compact unit for ease in packaging, product display, travel and storage, the headgear comprising a headband with cloth fabric sewed thereon; and a soft foam bill attached to said headband, said soft foam bill covered by cloth fabric sewed thereon, said soft foam bill characterized by being made of closed cell resin foam and having a density range of 5 to 12 pcf, whereby said soft foam bill, by the nature of the foam construction, won't break or crease when folded or crushed.

2. The headgear as described in claim 1 wherein the closed cell resin foam is from a family of polyolefin resin foam material and having an average cell size 0.008 inches.

3. The headgear as described in claim 1 wherein said soft foam bill has a thickness in a range of $3/32$ to $1/8$ inches.

4. The headgear as described in claim 1 wherein said soft foam bill has a compression set in a range of 6 to 10% of its thickness.

5. The headgear as described in claim 1 wherein said headband includes a first end with hook fasteners thereon and a second end with loop fasteners thereon, the hook and loop fasteners allowing the headgear to be adjustable on different size heads.

6. The headgear as described in claim 1 wherein said headband includes an open cell foam material therein and is designed to absorb perspiration and be self wicking.

7. A high quality, ultra-lightweight headgear adapted for folding and rolling into a tight compact unit for ease in packaging, product display, travel and storage, the headgear comprising:

a headband with cloth fabric sewed thereon; and a soft foam bill attached to said headband, said soft foam bill covered by cloth fabric sewed thereon, said soft foam bill characterized by being made of closed cell, polyolefin foam with an average cell size of 0.008 inches and a density range of 5 to 12 pcf, whereby said soft foam bill, by the nature of the polyolefin resin foam construction, won't break or crease when folded or crushed.

8. The headgear as described in claim 7 wherein said soft foam bill has a thickness in a range of $3/32$ to $1/8$ inches.

9. The headgear as described in claim 7 wherein said soft foam bill has a compression set in a range of 6 to 10% of its thickness.

10. The headgear as described in claim 7 wherein said headband includes a first end with hook fasteners thereon and a second end with loop fasteners thereon, the hook and loop fasteners allowing the headgear to be adjustable on different size heads.

11. The headgear as described in claim 7 wherein said includes an open cell foam material therein and is designed to absorb perspiration and be self wicking.

12. A method of folding and rolling a high quality, ultra-lightweight headgear comprised of the following steps:

providing a headgear having a headband and a soft foam bill attached to the headband wherein the headband and soft foam bill are covered by cloth fabric and wherein the soft foam bill is comprised of closed cell, polyolefin resin foam with an average cell size of 0.008 inches and a density range of 5 to 12 pcf;

folding the headband onto a portion of the soft foam bill; and rolling the headband and soft form bill into a tight compact unit for ease in packaging, a product display, travel and storage.

13. The method as described in claim 12 further including the step of rolling the headband and soft foam bill and returning the headgear to its original state after the steps of folding the headband and rolling the headband and soft foam bill into a tight compact unit.

14. The method as described in claim 12 further including a step of folding a headcover, the headcover being part of the headgear, on the headband and rolling the headcover, headband and soft foam bill into a tight compact unit.

15. The method as described in claim 12 further including the step of securing a tie around the rolled up tight compact unit of the headband and soft foam bill for holding the roll in place.

* * * * *